United States Patent [19]

DeMarzo

[11] Patent Number: 4,643,193
[45] Date of Patent: Feb. 17, 1987

[54] ECG ELECTRODE WITH SENSING ELEMENT HAVING A CONDUCTIVE COATING IN A PATTERN THEREON

[75] Inventor: Arthur P. DeMarzo, Wheaton, Ill.

[73] Assignee: C. R. Bard, Inc., Murray Hill, N.J.

[21] Appl. No.: 741,252

[22] Filed: Jun. 4, 1985

[51] Int. Cl.[4] .......................... A61N 1/04; A61B 5/04
[52] U.S. Cl. ...................................... 128/639; 128/640
[58] Field of Search ............... 128/639, 640, 641, 643, 128/798

[56] References Cited

U.S. PATENT DOCUMENTS

| | | | |
|---|---|---|---|
| 2,943,628 | 7/1960 | Howell | 128/640 |
| 3,474,775 | 10/1969 | Johnson | 128/639 |
| 3,572,322 | 3/1971 | Wade | 128/640 |
| 3,720,209 | 3/1973 | Boldue | 128/2.06 |
| 3,911,906 | 10/1975 | Reinhold, Jr. | 128/2.06 |
| 3,954,100 | 5/1976 | Sem-Jacobsen | 128/639 |
| 3,989,036 | 11/1976 | Sasamori | 128/640 |
| 4,082,087 | 4/1978 | Howson | 128/640 |
| 4,092,985 | 6/1978 | Kaufman | 128/303.13 |
| 4,354,509 | 10/1982 | Strahwald et al. | 128/639 |
| 4,365,634 | 12/1982 | Bare et al. | 128/640 |
| 4,375,219 | 3/1983 | Schmid | 128/644 |
| 4,391,278 | 7/1983 | Cahalan et al. | 128/798 |
| 4,543,958 | 10/1985 | Cartmell | 128/640 |

Primary Examiner—Edward M. Coven
Attorney, Agent, or Firm—Trexler, Bushnell & Wolters, Ltd.

[57] ABSTRACT

A medical electrode comprises a flat, resilient, electrically non-conductive backing member; a flat sensor element applied to one surface of the backing member and positioned for leaving a portion of this one surface exposed about a major portion of the periphery of the sensor element; and an electrically conductive coating applied to selected areas of the exposed surface of the sensing element.

17 Claims, 6 Drawing Figures

ECG ELECTRODE WITH SENSING ELEMENT HAVING A CONDUCTIVE COATING IN A PATTERN THEREON

BACKGROUND OF THE INVENTION

This invention relates to electrodes, and more particularly to disposable medical electrodes of the type employed in transcutaneous monitoring of biological or physiological electrical potentials associated with muscular activity.

Electrodes of the foregoing type are utilized in a number of applications for a variety of purposes. The monitoring of physiological electrical potentials to detect muscular activity of the heart muscle is generally well established, such apparatus being referred to in the art as an electrocardiograph (ECG) apparatus. The resulting traces or electrocardiogram obtained by this apparatus provide a diagnostic tool for detecting heart disease and/or defects. Such monitoring of physiological electrical potentials may of course be employed in a number of other applications. However, the electrode of the present invention will be described herein with particular reference to its use in connection with ECG apparatus.

Such ECG traces or electrocardiograms may be desired in a number of different situations. For example, a simple ECG test to obtain a single tracing for diagnostic purposes may be carried out in a few minutes in a physician's office. Hence, electrodes utilized for such testing may readily be of a relatively simple disposable variety, since they are only in service for a very short time.

On the other hand, longer term monitoring applications require the electrodes to remain in place on the patient's skin for considerably longer periods of time. For example, in stress testing, the heart activity of the patient is monitored over a relatively longer period of time while the patient exercises, for example upon a treadmill or the like. Such testing may include monitoring of the heart activity during the exercise, as well as continued monitoring during a rest period thereafter to monitor the return of the heart to a normal or unstressed condition.

Similarly, electrodes monitoring heart activity during surgery may be required to remain in place and operational for a period of several hours duration. In similar fashion, patients hospitalized in intensive care or other specialized care units may require around-the-clock monitoring. Hence, electrodes utilized for the ECG monitoring over such extended periods must remain in service for many hours and sometimes over a period of several days.

In most of the foregoing applications, two important and competing considerations must be addressed in designing a suitable electrode for ECG monitoring. Initially, it is desirable, especially during simple, short term ECG testing, to obtain a useful trace from the electrode as soon as possible after placing the electrode on the skin. Hence, initially placing and thereafter maintaining the electrode in intimate contact with the skin is an important consideration in rapidly obtaining a usable trace, as well as in maintaining the quality of the trace throughout the monitoring period. In this regard, the time required to obtain a useful trace is often referred to as "warm-up time". Maintaining good contact of the electrode with the skin is also important in avoiding motion artifacts, which generally comprise disturbances in the trace due to relative movement between the electrode and the skin, such as when the patient moves.

It has been found that the warm-up time and motion artifacts may be minimized by utilizing an electrically conductive coating such as a gel or an electrically conductive adhesive on the surface of the electrode in contact with the skin. In this way, an intimate electrical connection is achieved between the electrode and the skin of the patient through the intermediary of the electrically conductive gel or adhesive substance.

However, another important consideration, particularly with respect to longer term monitoring, such as in stress testing, during surgery or during in-patient hospital monitoring, is the recovery of the trace following defibrillation. That is, it sometimes becomes necessary to apply a relatively large externally generated electrical potential of short duration to the patient in an attempt to cause the heart to return to normal activity. The abnormal heart activity to be remedied by this procedure is referred to as fibrillation, and hence this application of electrical potential is often referred to as defibrillation. Since the electrocardiograph device measures electrical potential, such sudden application of large electrical potential will cause a considerable disturbance in the electrocardiogram trace. It has been found that when the monitoring electrode is in direct contact with the skin of the patient, the electrical charges built up during defibrillation tend to rapidly discharge between the skin and electrode, such that "recovery" of the electrocardiogram trace is relatively rapid.

However, it will be seen that the use of an electrically conductive gel or adhesive prevents the direct skin-to-electrode contact of the type conducive to rapid recovery from defibrillation. In response to these competing considerations, the prior art has developed a relatively complex and expensive silver/silver chloride electrode system. This system has been developed in an effort to accommodate both of the foregoing considerations. Typically, such a system utilizes a sensing element or portion of the electrode which has a silver chloride surface that interfaces with an electrically conductive chloride gel interposed between the sensing element surface and the skin of the patient. The defibrillation recovery is then enhanced by a silver/silver chloride chemical reaction involving the silver chloride on the sensing element and the chloride of the gel. This reaction tends to dissipate the electrical charge relatively rapidly. However, the manufacture of such electrodes and gels and the further manufacture or assembly thereof into prepackaged, disposable electrodes, utilizing this silver/silver chloride technology, is relatively difficult and expensive.

OBJECTS AND SUMMARY OF THE INVENTION

Accordingly, it is a general object of the invention to provide a novel and improved medical electrode.

A more specific object is to provide an improved ECG electrode which accommodates the competing considerations of minimizing warm-up time and motion artifacts while facilitating defibrillation recovery as discussed hereinabove.

A related object is to provide an electrode in accordance with the foregoing objects which is relatively simple and inexpensive compared to the silver/silver chloride technology discussed hereinabove, and yet is highly reliable in operation.

Briefly, and in accordance with the foregoing objects, a medical electrode according to the invention comprises a non-conductive backing member; a flat sensor element applied to one surface of said backing member; and a coating applied to selected areas of the exposed surface of said sensing element, which coating will hold the uncoated portions of the sensor element in intimate contact with the skin of a patient, the coating may be conductive which establishes electrical contact between the patients skin and the coated portions of the sensor elements and may be a conductive adhesive or a conductive gel.

BRIEF DESCRIPTION OF THE DRAWINGS

The features of the present invention which are believed to be novel are set forth with particularity in the appended claims. The organization and manner of operation of the invention, together with further objects and advantages thereof, may best be understood by reference to the following description taken in connection with the accompanying drawings in the several figures of which like reference numerals identify like elements, and in which:

DETAILED DESCRIPTION OF THE ILLUSTRATED EMBODIMENT

Figure 1:
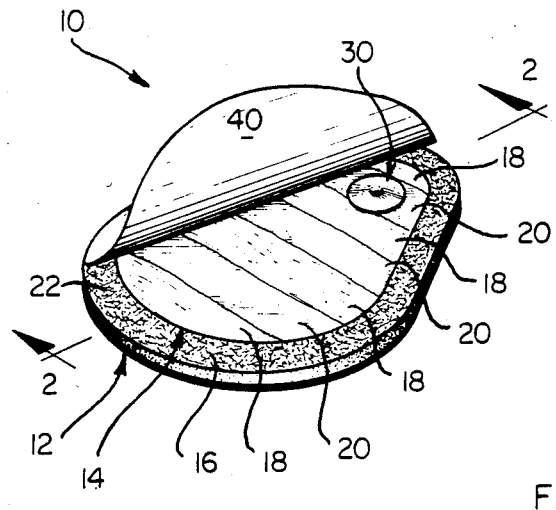
FIG. 1 is a perspective view of an ECG electrode in accordance with one embodiment of the invention.
Figure 2:
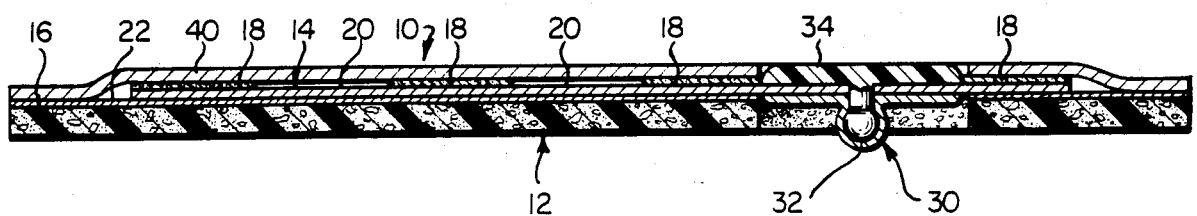
FIG. 2 is an enlarged sectional view taken generally in the plane of the line 2—2 of FIG. 1.

Referring to the drawings, and initially to FIGS. 1 and 2, an ECG electrode in accordance with one embodiment of the invention is designated generally by the reference numeral 10. The electrode 10 includes a substantially flat, sheet-like backing member 12 of an electrically non-conductive material. Preferably, this non-conductive material is a foam-like material, for example, a polyethylene foam material.

A generally flat, electrically conductive sensing element 14 is applied to one surface of the backing member 12, this sensing element 14 being of generally smaller transverse dimensions than the backing member 12. Moreover, the sensing element 14 is preferably positioned such that the aforementioned one surface of the backing member is exposed about a major portion of the periphery of the sensing element 14, as indicated generally at reference numeral 16. In accordance with the FIG. 1 embodiment of the invention, an electrically conductive coating 18 is applied to the exposed surface of the sensing element in a predetermined pattern, such that selected areas of the sensing element are covered with this conductive coating 18 and other selected areas, for example as indicated at reference numeral 20, are substantially free of this conductive coating 18.

In the illustrated embodiment, a quantity of adhesive material, indicated generally at 22, is applied to the surface of the backing member for adhering both to the sensing element and to the skin of a patient in the area 16 about the periphery of the sensing element 14. Preferably, this adhesive 22 comprises a pressure sensitive adhesive material. In this regard, the indication of the relative thicknesses of the adhesive layer 22, as well as that of the sensing element 14 and coating 18 have been exaggerated to facilitate illustration thereof.

In accordance with one feature of the invention, the conductive coating 18 may comprise an electrically conductive adhesive material for adhering to the skin of the patient, and may be of a type and kind well known in the art. Alternatively, the coating 18 may comprise an electrically conductive gel material for promoting enhanced electrical contact between the skin of the patient and the facing surface of the sensing element 14. As mentioned above, the provision of such conductive contact by way of electrically conductive gel or adhesive material minimizes warm-up time and maintains the quality of the trace throughout the monitoring. Moreover, the intimate contact between the uncoated portion 20 and the patients skin achieved by use of such an intermediary material aids in avoiding motion artifacts, that is, disturbances in the trace due to relative movement between the electrode and the skin.

On the other hand, in order to facilitate relatively rapid defibrillation recovery, as also discussed above, substantial areas 20 of the sensing element are left free of the coating 18. These latter areas 20 promote relatively rapid electrical discharge of the charges which would otherwise build up during defibrillation, thus permitting a relative rapid resumption of a usable ECG trace from the electrode.

Thus, upon the application of the electrode 10 to a patient, the uncoated portions or areas 20 of the sensing element 14 will be held in direct surface-to-surface contact with the patients skin, as the coated areas 18 prevent the uncoated areas 20 from bowing or gapping away from the patients skin. The coating 18 is preferably conductive and establishes an electrical path between the patients skin and the underlying areas of the sensor element 14, which assures attainment of a trace pattern as soon as the electrode is applied. Further, the prevention of gapping or bowing of the uncoated portions precludes disruptions in the circuit path during patient movement, and as such resists motion artifacts. Further, with the uncoated areas 20 held in intimate contact with the patients skin by the coating 18, the electrode 10 will dissipate rapidly any electrical charge that may be created during defibrillation.

The electrode 10 is thus possessed with rapid recovery characteristics after defibrillation, as well as having excellent warm-up characteristics and resistance to motion artifacts. By varying the relative sizes of the coated and uncoated areas, the respective characteristics of the electrode can be selected as desired. Most importantly, the advantages noted above are achieved with a simple and economical structure, as compared with the prior art design which utilize a silver/silver chloride type of system.

In the embodiment illustrated in FIG. 1, the electrically conductive coating is applied to the sensing element 14 in generally parallel, spaced apart stripes extending transversely thereacross to define a pattern thereon. Moreover, these stripes 18 are substantially uniformly spaced, that is, the uncoated areas 20 therebetween are of substantially uniform width. Preferably, at least portions of these stripes as shown in cross-section in FIG. 2, are also of substantially similar or uniform width.

In the embodiment illustrated in FIG. 1, both the sensor element 14 and the backing member 12 define, over a major fractional portion of their respective peripheries, peripheral shapes which are substantially geometrically similar. The sensor element is of lesser transverse dimensions than the backing member and is substantially centered with respect thereto so as to define the peripherally exposed, and preferably adhesive-coated, portion 16 of the backing member 12.

Additionally, the embodiment of FIGS. 1 and 2 include an electrical connector member 30 which is both physically and electrically coupled with the sensing element 14 for receiving a mating electrical connector. In the illustrated embodiment, the connector element 30 comprises the male portion or half of a snap-type connector. This male connector element or member 30 generally comprises an operative or connector portion 32 and a complementary securing or mounting portion 34 for securing the operative portion 32 to the sensor element 14. In this regard, the two connector portions 32 and 34 may be advanced toward each other from opposite sides of the flat sensing element 14, with the securing portion 34 being advanced therethrough and into engagement with the operative portion 32 to grip the generally flat sensing element 14 therebetween.

In the embodiment illustrated in FIGS. 1 and 2, an additional, peelable or stripable protective cover member or strip 40 is also provided. As shown in FIG. 2, this peelable cover 40 preferably comprises a thin sheet of release liner material which is releasably adhered to the adhesive 22 about the peripheral surface portion 16 of the backing 12, so as to form a protective covering for the electrode 10 prior to use. When it is desired to use the electrode 10, this peelable cover member 40 may be peeled back and removed in the fashion generally indicated in FIG. 1.

Figure 3:
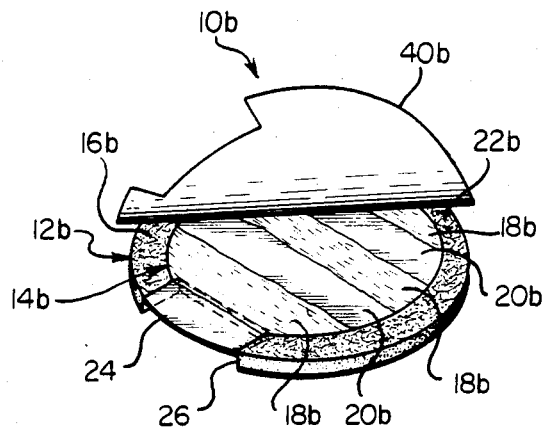
FIG. 3 is a perspective view of an ECG electrode in accordance with another embodiment of the invention.

Referring next to FIG. 3, an alternate embodiment of an ECG electrode in accordance with the invention is designated generally by reference numeral 10b. The electrode 10b is substantially similar in construction to the electrode 10 of FIGS. 1 and 2, and hence like reference numerals with the subscript b are utilized in FIG. 3 to indicate similar elements and components. In this regard, the electrode 10b includes a backing member 12b also preferably of a polyethlyene foam material. A sensing element 14b is adhered to an adhesive layer 22 on the backing member 12b so as to leave a portion 16b of the surface thereof exposed about a major portion of the periphery of sensing element 14b. A release liner, peelable cover 40b is also provided. In similar fashion to the embodiment of FIG. 1, a conductive coating which may comprise a conductive gel or a conductive adhesive is applied in a pattern as indicated by reference numerals 18b, to the surface of the sensing element 14b.

Preferably, this pattern comprises a plurality of stripes of the conductive coating 18b which are of substantially similar width and are parallel and spaced apart by substantially similar spaces comprising uncoated areas 20b of the sensing element 14b.

Like the embodiment of FIGS. 1 and 2, the major peripheral portions of both sensing element 14b and backing 12b define substantially geometrically similar shapes and the sensing element is of lesser transverse dimensions than and substantially centered with respect to the backing member. However, an additional outwardly extending tab-like extension portion 24 is provided on sensing element 14b for receiving an electrical connector or connector means, such as an alligator clip or the like. This tab-like extension 24 extends over a complementary shaped cutout portion 26 of the backing member 12a to provide a substantial portion thereof for receiving such an electrical connector. In this regard, the surfaces of the tab-like extension 24 are preferably left uncoated by the conductive adhesive or conductive gel coating 18b.

In the embodiments illustrated in FIGS. 1 and 2 and in FIG. 3, the sensing element 14, 14b preferably comprises a conductive plastic material. For example, a carbon-filled polyvinyl chloride material may be utilized to form the sensing element.

Figure 4:
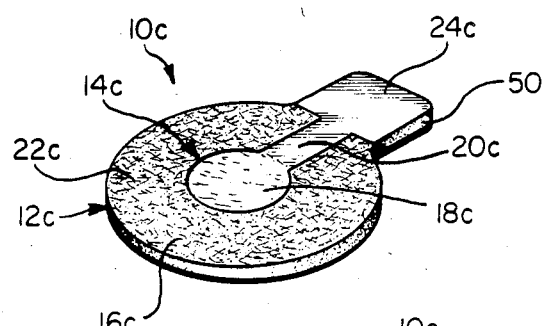
FIG. 4 is a perspective view of an ECG electrode in accordance with another embodiment of the invention.
Figure 5:
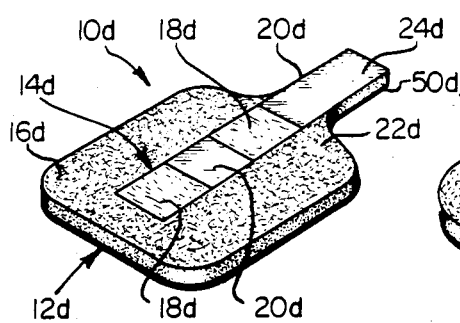
FIG. 5 is a perspective view of an ECG electrode in accordance with another form of the invention.

Referring next to FIGS. 4 and 5, electrodes 10c and 10d of somewhat different shape, and preferably of somewhat smaller dimensions, but also configured in accordance with the invention, are illustrated. These electrodes are also substantially similar in their overall construction to the electrodes described hereinabove. Hence, similar reference numerals, with respective subscripts c and d will be utilized to indicate the similar parts and components thereof.

Intially, it will be noted that the electrodes illustrated in FIGS. 1, 2 and 3 are of suitable dimensions and configuration for relatively long term ECG monitoring, for example during surgery or for long-term patient care. However, the electrodes of FIGS. 4 and 5 are of a somewhat simplified construction, and of generally smaller size. Hence, these latter electrodes are intended primarily for use in short-term ECG testing, that is, for obtaining a test trace over a relative short period of time. In this regard, the electrodes of FIGS. 1 and 3 have been illustrated somewhat smaller than actual size, while the electrodes of FIGS. 4 and 5 have been illustrated somewhat larger than actual size to facilitate their presentation herein for exemplary purposes.

Referring now more particularly to FIGS. 4 and 5, electrodes 10c and 10d each comprise a non-conductive and preferably a polyethylene foam material backing member 12c, 12d. In similar fashion to the previously described embodiments, the electrodes of FIGS. 4 and 5 also include relatively flat sensing elements 14c, 14d of smaller transverse dimension than the backing members 12c, 12d. Preferably, at least substantial portions of the sensing elements 14c and 14d are of a generally geometrically similar configuration or peripheral shape to the backing members 12c, 12d and are substantially centered with respect thereto. This then leaves substantial peripheral surface areas of the backing members 12c, 12d exposed as indicated generally at 16c, 16d. Preferably, the surfaces of the backing members, including areas 16c, 16d, are covered with an adhesive material 22c, 22d to adhere the respective sensing members thereto and also to adhere to the skin of the patients in the areas 16c and 16d.

In accordance with the invention, the embodiments of FIGS. 4 and 5 include electrically conductive coatings 18c, 18d applied to selected portions of the sensing elements thereof in a predetermined pattern. These coatings are applied such that selected areas of each of the sensing elements 14c, 14d are covered with the conductive coating and other selected areas, as indicated by reference numerals 20c and 20d, are left uncovered by the conductive coating. This coating may comprise either an electrically conductive adhesive material or an electrically conductive gel material.

Departing somewhat from the embodiments previously described, the embodiments of FIGS. 4 and 5 utilize a relatively thin, metallic foil material, and preferably an aluminum foil material, to form the sensing elements 14c, 14d. In this regard each of the sensing elements further includes a connector tab portion 24c, 24d which extend substantially to an edge of the backing member. However, in both electrodes 10c and 10d the backing member 12c, 12d is also formed with an extension or connector tab portion 50d, of substantially similar configuration and area to the connector tab portion or extension 24e, 24d for receiving and supporting the latter.

Figure 6:
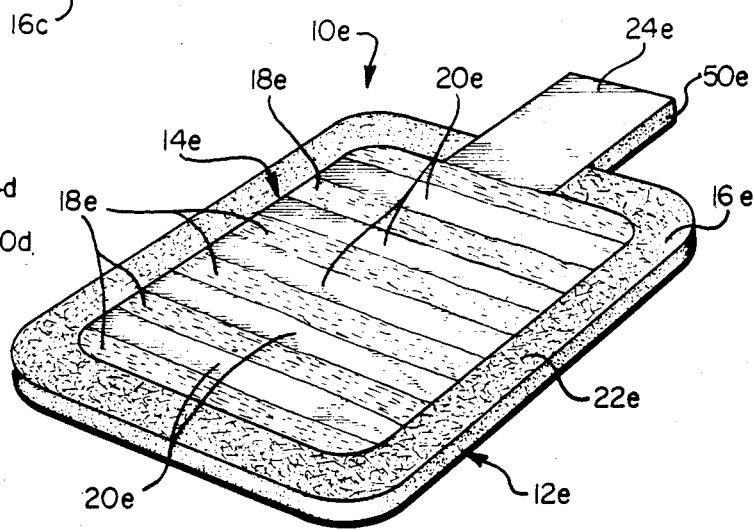
FIG. 6 is a perspective view of a relatively large, dispersive-type of ECG electrode in accordance with yet another embodiment of the invention.

Reference is next invited to FIG. 6, wherein yet another embodiment of an electrode 10e in accordance with the invention is illustrated. The electrode 10e of FIG. 6 preferably comprises a dispersive-type of electrode, which is of considerably greater transverse dimensions than the electrodes previously described herein. Such an electrode is utilized generally as a "grounding pad" to provide a relatively large effective electrical ground area for the grounding of the patient. Such a grounding pad is preferably utilized in surgical applications, wherein relatively long term monitoring is desired. The overall peripheral shape or configuration of the grounding pad of FIG. 6 is substantially rectilinear, although other shapes or configurations may be utilized without departing from the invention. In this regard, the various parts, elements and components of grounding pad 10e are substantially similar to those of the electrodes previously described, whereby like reference numerals with the subscript e are utilized to designate such similar parts.

In this regard, a backing member 12e, preferably of a polyethylene foam material, receives a sensing element 14e, preferably affixed thereto by means of an adhesive material 22e. The major portion of sensing element 14e is of substantially geometrically similar peripheral configuration and of smaller transverse dimensions than pad 12e and is substantially centered with respect thereto to leave a substantial peripheral area 16e exposed for adhering to the skin of the patient. In the embodiment illustrated in FIG. 6, the sensing element 14e comprises a metallic foil and preferably aluminum foil material. In accordance with the invention, an electrically conductive coating 18e is applied in a pattern to selected areas of the sensing element 14e, leaving other selected areas 20e exposed or free of coating 18e. In the embodiment illustrated, it will be seen that coating 18e is applied in a plurality of strips or stripes which are of generally uniform width and spaced apart uniformly by areas 20e, in somewhat the same fashion as previously described with respect to the embodiments of FIGS. 1 and 3. Also in accordance with the previously described embodiments, the conductive coating 18e may comprise either a conductive adhesive material or a conductive gel material.

In a fashion similar to the embodiments of FIGS. 4 and 5, both the backing member 12e and the sensing element 14e have substantially coextensive extension portions or tab portions 24e, 50e which extend outwardly of the main bodies thereof, for example for receiving electrical connectors for coupling to an electrosurgical apparatus. Also, the electrodes 10c, 10d and 10e of FIGS. 4, 5 and 6 are preferably provided with peelable covers of release liner material similar to covers 40, 40b of FIGS. 1, 2 and 3. However, these covers have been omitted in FIGS. 4, 5 and 6 for clarity.

While particular embodiments of the invention have been shown and described in detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiment and specific construction described herein but should be defined by the appended claims and equivalents thereof. Accordingly, the aim in the appended claims is to cover all such changes and modifications as fall within the true spirit and scope of the invention.

The invention is claimed as follows:

1. A medical electrode comprising: a backing member having an adhesively coated surface, sensor means affixed to said backing member and being of a lesser overall dimension such that said adhesively coated surface of the backing member is exposed about a substantial portion of the periphery of said sensor means, said sensor means being formed of an electrically conductive material and having a flat, electrically condutive surface portion for engagement with the skin of a patient, and an electrically conductive coating applied to selected areas of said flat surface portion of said sensor means such that areas of said surface portion other than said coated selected areas are substantially free of said conductive coating, thereby defining a predetermined pattern on said flat surface portion of said sensor means of areas having said conductive coating applied thereto and areas substantially free of said conductive coating, respectively, such that upon application of the electrode to a patient the exposed portion of said adhesively coated surface of the backing member will hold the sensor means in contact with the patient's skin whereby those areas of said surface portion that are free of said conductive coating will be brought into electrically conductive surface-to-surface contact with the patient's skin, while the coated areas of said surface portion will be in electrical contact with the patient's skin by means of said conductive coating.

2. A medical electrode according to claim 1 wherein said conductive coating comprises an electrically conductive adhesive material.

3. A medical electrode according to claim 1 wherein said conductive coating comprises an electrically conductive gel material.

4. A medical electrode according to claim 1 wherein said conductive coating is applied to said sensing means surface portion in parallel, spaced apart stripes to define said predetermined pattern.

5. A medical electrode according to claim 1 wherein said sensing means comprises a conductive plastic material.

6. A medical electrode according to claim 5 wherein said conductive plastic material comprises a carbon-filled polyvinyl chloride material.

7. A medical electrode according to claim 1 wherein said sensing means comprises a metallic foil material.

8. A medical electrode according to claim 7 wherein said metallic foil material comprises an aluminum foil material.

9. A medical electrode according to claim 1 wherein said sensing means includes a connector tab portion extending substantially to a peripheral edge of said backing member.

10. A medical electrode according to claim 1 wherein said backing member comprises a polyethylene foam material.

11. A medical electrode according to claim 1 wherein said adhesive material applied to said backing member comprises a pressure sensitive adhesive.

12. A medical electrode according to claim 1 wherein said sensing means includes a tab-like extension portion and wherein said backing member includes a cutout portion into which said tab-like extension portion extends for receiving electrical connector means.

13. A medical electrode according to claim 1 and further including an electrical connector element coupled with said sensing for receiving a mating electrical connector.

14. A medical electrode according to claim 1 wherein said predetermined pattern comprises a plurality of parallel stripes of said coating extending transversely across said sensing means, said stripes being respectively substantially uniformly spaced.

15. A medical electrode according to claim 1 wherein said sensing means and said backing member define over a major fractional portion of the peripheries thereof peripheral shapes which are substantially geometrically similar, and wherein said sensing means is of lesser transverse dimensions than and substantially centered with respect to said backing member.

16. A medical electrode comprising: a sensor element formed of an electrically conductive and having a flat, electrically conductive surface portion for engagement with the skin of a patient, and an electrically conductive coating applied to selected areas of said flat surface portion of said sensor element such that areas of said surface portion other than said coated selected areas are substantially free of said conductive coating, thereby defining a predetermined pattern on said flat surface portion of said sensor element of areas having said conductive coating applied thereto and areas substantially free of said conductive coating, respectively, said conductive coating comprising an electrically conductive, pressure sensitive adhesive material, with at least one or more of said uncoated areas being disposed intermediate an area or areas having said conductive adhesive thereon such that upon application of the electrode to a patient the pressure sensitive adhesive will hold the surface portion of said sensor element in contact with the patient's skin with those areas of the surface portion that are free of said conductive coating being held in electrically conductive surface-to-surface contact with the patient's skin, while the coated areas of the surface portion will be in electrical contact with the patient's skin by means of said conductive adhesive coating.

17. A medical electrode according to claim 16 and further including a backing member having a substantially flat surface, said sensor element being applied to said flat surface of said backing member.

* * * * *